United States Patent
Vikman et al.

(10) Patent No.: US 10,683,120 B2
(45) Date of Patent: Jun. 16, 2020

(54) STERILIZATION PACKAGING, A METHOD FOR PACKAGING A PRODUCT THEREIN, AND A METHOD FOR THE REMOVAL OF A PRODUCT FROM SAID PACKAGING

(71) Applicant: WIPAK B.V., Sittard (NL)

(72) Inventors: Jouni Matias Vikman, Nastola (FI); Paavo Petteri Muhonen, Nastola (FI); Kai Nieber, Bomlitz (DE); Michael Stephanus Terwolbeck, Sittard (NL)

(73) Assignee: WIPAK B.V., Sittard (NL)

( * ) Notice: Subject to any disclaimer, the term of this patent is extended or adjusted under 35 U.S.C. 154(b) by 315 days.

(21) Appl. No.: 15/492,970

(22) Filed: Apr. 20, 2017

(65) Prior Publication Data

US 2017/0217618 A1    Aug. 3, 2017

Related U.S. Application Data

(63) Continuation of application No. PCT/NL2015/050734, filed on Oct. 22, 2015.

(30) Foreign Application Priority Data

Oct. 23, 2014  (NL) ................................ 2013669

(51) Int. Cl.
  *B65B 55/16* (2006.01)
  *B65D 75/58* (2006.01)
  (Continued)

(52) U.S. Cl.
  CPC .............. *B65B 55/16* (2013.01); *A61L 2/081* (2013.01); *A61L 2/206* (2013.01); *A61L 2/26* (2013.01);
  (Continued)

(58) Field of Classification Search
  CPC ......... B65B 55/18; B65B 55/16; B65B 55/02; B65B 7/02; A61L 2/081; A61L 2/26; A61L 2/206; A61L 2202/181; B65D 75/30; B65D 75/566; B65D 75/5855; B65D 75/2084; B65D 75/263
  (Continued)

(56) References Cited

U.S. PATENT DOCUMENTS

| | | |
|---|---|---|
| 3,768,725 A | 10/1973 | Pilaro |
| 2011/0211991 A1 | 9/2011 | Foltz et al. |
| 2013/0203576 A1 | 8/2013 | Daughtry et al. |

FOREIGN PATENT DOCUMENTS

| | | |
|---|---|---|
| EP | 1550466 | 7/2005 |
| JP | 2010-268967 | 12/2010 |

(Continued)

*Primary Examiner* — Ruiyun Zhang
(74) *Attorney, Agent, or Firm* — Peacock Law P.C.; Janeen Vilven

(57) ABSTRACT

Packaging for sterile packaging a product, comprising a bag shaped body with two main surfaces that are mutually gas tight at at least part of their peripheral edges comprising a gas non-permeable material. At least part of the main surfaces comprises a gas permeable material part of a pore size that locks out harmful organisms and comprises a gas tight material part that is positioned between two peripheral edges that extend in a longitudinal direction and between the gas permeable material part and a peripheral edge that extends in a transverse direction.

17 Claims, 2 Drawing Sheets

(51) Int. Cl.
*B65D 75/56* (2006.01)
*B65D 81/20* (2006.01)
*B65D 81/26* (2006.01)
*B65B 55/02* (2006.01)
*A61L 2/08* (2006.01)
*A61L 2/20* (2006.01)
*A61L 2/26* (2006.01)
*B65B 7/02* (2006.01)
*B65B 55/18* (2006.01)
*B65D 75/30* (2006.01)

(52) U.S. Cl.
CPC ............ *B65B 7/02* (2013.01); *B65B 55/02* (2013.01); *B65B 55/18* (2013.01); *B65D 75/30* (2013.01); *B65D 75/566* (2013.01); *B65D 75/5855* (2013.01); *B65D 81/2084* (2013.01); *B65D 81/263* (2013.01); *A61L 2202/181* (2013.01)

(58) Field of Classification Search
USPC ............ 428/34.1, 34.3, 34.6, 36.5; 493/189; 206/439, 484.1; 383/210, 200
See application file for complete search history.

(56) References Cited

FOREIGN PATENT DOCUMENTS

JP 2010268967 A * 12/2010
WO 2016/064274 4/2016

\* cited by examiner

STERILIZATION PACKAGING, A METHOD FOR PACKAGING A PRODUCT THEREIN, AND A METHOD FOR THE REMOVAL OF A PRODUCT FROM SAID PACKAGING

CROSS-REFERENCE TO RELATED APPLICATIONS

This application is a continuation application of Patent Cooperation Treaty Application No. PCT/NL2015/050734, filed on Oct. 22, 2015, which claims priority to Netherlands Patent Application No. 2013669, filed on Oct. 23, 2014, and the specifications and claims thereof are incorporated herein by reference.

STATEMENT REGARDING FEDERALLY SPONSORED RESEARCH OR DEVELOPMENT

Not Applicable.

THE NAMES OF PARTIES TO A JOINT RESEARCH AGREEMENT

Not Applicable.

INCORPORATION BY REFERENCE OF MATERIAL SUBMITTED ON A COMPACT DISC

Not Applicable.

STATEMENT REGARDING PRIOR DISCLOSURES BY THE INVENTOR OR A JOINT INVENTOR

Not Applicable.

COPYRIGHTED MATERIAL

Not Applicable.

BACKGROUND OF THE INVENTION

Field of the Invention (Technical Field)

The present invention relates to a packaging for sterile packaging a product, a method for sterile packaging a product in this packaging, and a method for removing a sterile packed product from the packaging.

Description of Related Art Including Information Disclosed Under 37 C.F.R. §§ 1.97 and 1.98

Such packaging is known in the art. For example, use is regularly made of a bag shaped packaging comprising a gas permeable surface. Said gas permeable surface serves as an access opening for removing said product that was packaged in said packaging. The seal that connects the gas permeable material with the other packaging materials must be torn.

Such packaging has the disadvantage that a large force is required for opening the packaging. Since the gas permeable part of the packaging usually is positioned at a central part of a main surface of the packaging, only a small opening is made in said packaging, requiring at least part of the packaging to be torn as well so as to be able to remove the contents from the packaging.

Therefore, there is a need for an improved packaging.

BRIEF SUMMARY OF THE INVENTION

The invention therefore aims at providing an improved packaging of the kind mentioned in the preamble.

More in particular, the invention aims at providing a packaging of the kind mentioned in the preamble that allows an easy removal of a product from the packaging.

The invention also aims at providing a packaging that can be easily transported.

Further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE SEVERAL VIEWS OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more embodiments of the invention and are not to be construed as limiting the invention. In the drawings.

DETAILED DESCRIPTION OF THE INVENTION

Figure 1:
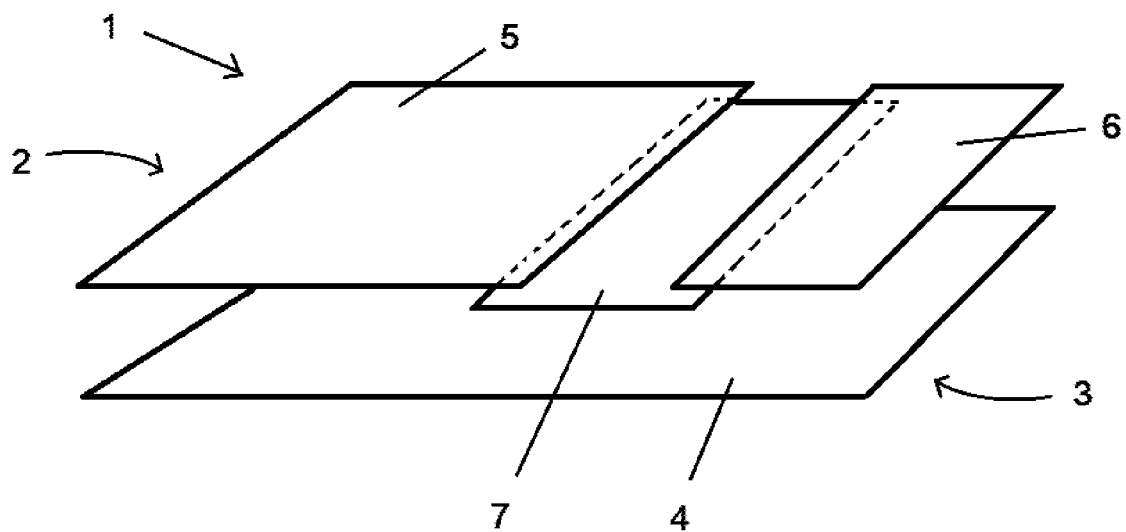
FIG. 1 is a schematic explosion view of a part of a packaging according to the invention.

So as to obtain at least one of the above identified aims, according to a first embodiment the invention provides a packaging comprising the features of claim 1. The packaging according to the invention comprises a bag shaped body comprising two main surfaces that are connected mutually gastight at at least part of their peripheral edges comprising a for gas non permeable material, wherein at least part of said main surfaces on the one hand comprises a gas permeable material part of a pore size that locks out harmful organisms, and on the other hand comprises a gastight material part that is positioned between two peripheral edges that extend in a longitudinal direction and between said gas permeable material part and a peripheral edge that extends in a transverse direction. The packaging is characterized in that said gas tight material part is releasably connected to said peripheral edges that extend in a longitudinal direction and to said gas permeable material; or in that said gas permeable material is rigidly connected to said gas tight material part and releasably connected to said gas tight material part; and wherein said gas permeable material part and said gas tight material part are releasably connected at peripheral edges. This packaging has the advantage that a very large opening can be created for removing the product from the packaging.

A first main surface of the packaging is preferably at least partly made from a gas permeable material. The other, second, main surface may be made completely from a gas non-permeable material. The remaining part of said first main surface may for example be made from the same material as the second main surface. That material, hereinafter also identified as "packaging material", is preferably a material that is both suitable for heat sealing and for providing a mutually releasable connection, like a releasable or peel-off connection.

A gas permeable material that is applicable within the present invention is Tyvek (registered trademark of E.I. DuPont de Nemours & Company), for example Tyvek 1073B, 1059B or 4058B (Tyvek 2FS). The invention is however not limited to Tyvek materials. Other brands and types of materials may be used. A requirement is that the said material is permeable to a sterilizing gas but non-permeable to (harmful) organisms. An advantage of said Tyvek material is its suitability for heat sealing, which allows a very strong bond with the other parts to be obtained. Furthermore, it is suitable for providing a releasable, for example a peelable or peel-off, connection with another plastic material, allowing to obtain a simple releasable connection.

According to the invention it is possible to provide the packaging with a handgrip which allows one to carry the packaging together with its contents simply and safely. Since the packaging adjacent to said gas permeable material part, at the side opposite the releasably connected material parts, will remain closed, that part may be made extremely strong, for example by mutually connecting said both main surfaces by means of heat sealing. As a consequence, that position will be made sufficiently strong for providing a handgrip, preventing any damage due to tearing or the like failure of the packaging.

As a consequence, preference is given to a packaging comprising a grip device for carrying the packaging adjacent to, or alongside, said gas permeable material part, at the side opposite the releasably connected material parts.

So as to ensure a suitable sterile treatment of the products packaged in said packaging, it is preferred that the peripheral edge comprises a foldable edge.

So as to be able to easily grip the parts of the packaging s as to mutually release them it is preferred that said gas permeable material part is positioned at an inside of said gas tight material part and at a distance from the peripheral edge of said gas permeable material part has been connected thereto.

It is especially preferred that a part of the peripheral edge of said main surface furthermore comprises a material that is sealable with said other main surface. Such provides the possibility of closing the packaging quickly, simply and adequately after entering a product that has to be packaged sterile in the packaging.

It is preferred for the sealable material to comprise a material that is fit for thermosealing (also known as "heat sealing"). For example, the respective parts of both main surfaces may comprise a coating and/or a so-called "seal layer" or they may be treated, so as to allow a heat sealing of said parts.

The edges that are connected by means of heat sealing (hereinafter also identified as "sealed edges") will be mutually connected substantially inseparably and gastight, which means that only by tearing or breaking one or both material parts at said sealed edge a dislocation of said both main surfaces may be obtained.

Within the invention, the terms "releasable" and "peelable" mean that two material parts may be separated from each other without substantially breaking the said material parts. Only a connecting layer, if applicable, connecting said both material parts will be destroyed or will be peeled off from one of both material parts. It is especially preferred that the releasable connection comprises a peelable connection; in the art such connection usually is identified as a "peelable" or "peel off" connection.

Said two edges that extend in a longitudinal direction are two opposite longitudinal edges of said packaging. However, as a matter of fact, the orientation of the packaging may be such that the opposite edges may be considered to be transverse edges. Within the description of this invention it is considered however that these opposite edges are longitudinal edges.

A simple structure of the packaging is obtained, comprising an ample surface of said gas permeable material part such that sterilization will be obtained easily, when said gas permeable surface substantially extends between two longitudinal edges of the packaging along the width of a first main surface of said packaging.

The term "width of the packaging" relates to the direction perpendicular to the longitudinal direction, as mentioned above.

A sturdy connection of said both main surfaces is obtained when said peripheral edge of said packaging, extending in a transverse direction, is embodied for providing a fixed connection of said both main surfaces. For example, a user can place a product that must be packaged sterile in the packaging, and subsequently close the packaging along said transverse peripheral edge by means of heat sealing. This allows one to close the packaging, wherein a gas may only leave the packaging through said gas permeable material part. All peripheral edges are closed off in a gas tight manner.

As a consequence, it is preferred that said transverse peripheral edge of said packaging provides a fixed connection of said both main surfaces by means of heat sealing.

According to a further aspect, the invention also relates to sterile closed packaging according to any of the preceding claims, comprising a sterile product.

According to a still further aspect, the invention relates to a method for sterile packaging a product in a packaging according to any of the preceding claims, comprising the steps of providing a packaging that comprises a bag shaped body comprising two main surfaces that are connected mutually gastight at at least part of their peripheral edges a for comprising a for gas non permeable material, wherein at least part of said main surfaces on the one hand comprises a gas permeable material part of a pore size that locks out harmful organisms, and on the other hand comprises a gastight material part that is positioned between two peripheral edges that extend in a longitudinal direction and between said gas permeable material part and a peripheral edge that extends in a transverse direction, characterized in that said gas tight material part is releasably connected to said peripheral edges that extend in a longitudinal direction and to said gas permeable material; or in that said gas permeable material is rigidly connected to said gas tight material part and releasably connected to said gas tight material part; and wherein said gas permeable material part and said gas tight material part are releasably connected at peripheral edges; and wherein said method further comprises the steps of: placing in the packaging through a non-connected peripheral edge a product that is to be sterile packed, mutually connecting said non-connected peripheral edges, and sterilizing the contents of the packaging.

Sterilizing the contents may for example be made by at least one of the steps of: subjecting to gamma radiation at least said product, and—entering a sterilization gas into said packaging through said gas permeable surface. Said sterilizing gas may suitably be comprised of ETO gas, that can be simply brought into the packaging through the ores of the Tyvek material. The pores of said material that is permeable to said sterilization gas therefore need to be sufficient large to be able to bring said sterilization gas into the packaging. A man skilled in the art will be easily capable of determining other materials than the types of Tyvek material as mentioned above, for application in the present invention.

The sterilization gas may be easily and effectively brought into the packaging by the steps of firstly at least partially evacuating the packaging and subsequently entering said sterilization gas through said gas permeable surface.

So as to remove a sterilized product from a sterile packaging according to the invention preferably the following steps are performed: releasing a part of said both main surfaces along a peripheral edge of said packaging; releasing a connection edge of said gas tight material part with said gas permeable material part or a connection edge of said gas permeable material part with a material part that is connected thereto; unfolding said packaging along a non-released peripheral edge; and removing said sterile product from the opened packaging.

According to a preferred embodiment said released part of a first main surface of said packaging remains connected with said other main surface along the edge, so as to obtain a sturdy connection providing a high strength, allowing one to carry the packaging by means of said hand grip.

The invention will now be explained by way of the drawings. In the figures the same parts are identified by the same reference numerals. However, not all parts that are required for a practical embodiment of the invention are shown for ease of understanding the figures.

Figure 3:
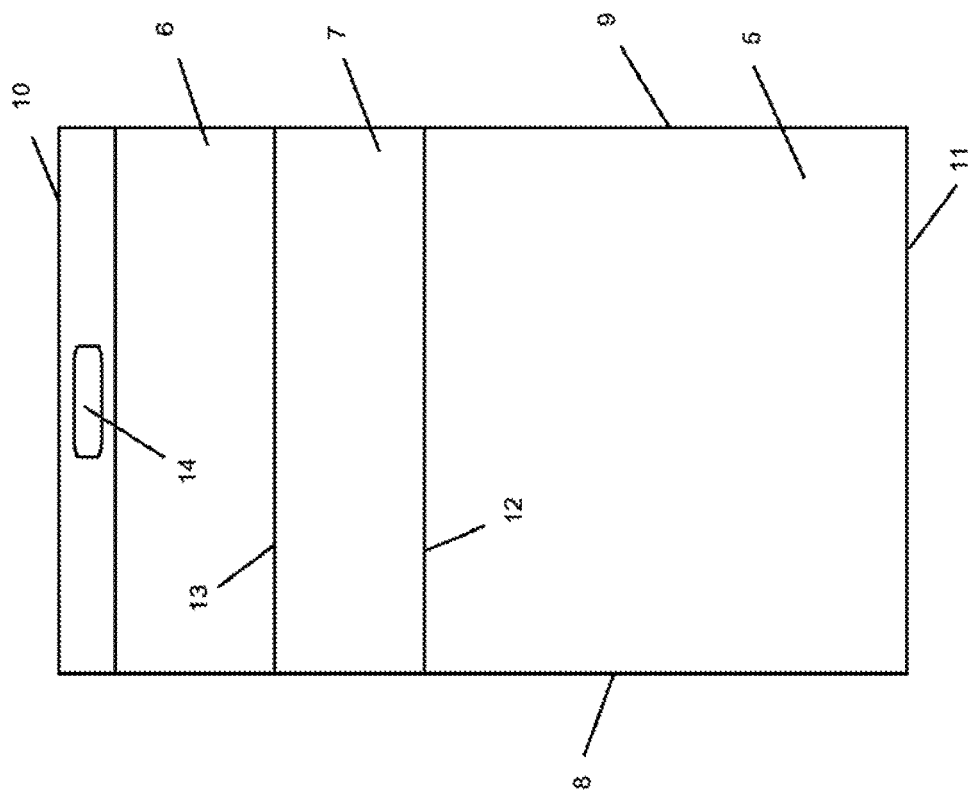
FIG. 3 is a front view of a second embodiment of a packaging according to the invention.
Figure 2:
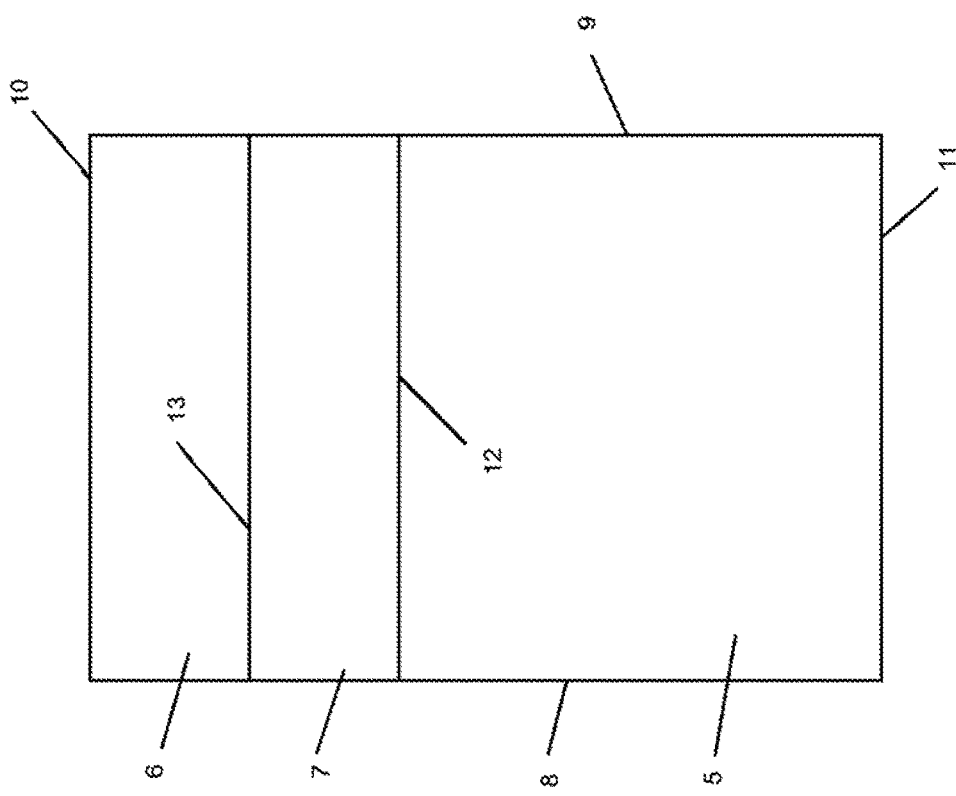
FIG. 2 is a front view of a first embodiment of a packaging according to the invention.

FIG. 1 shows a schematic explosion view of part of a packaging 1 according to the invention. The packaging 1 comprises a first main surface 2, as shown in FIG. 2 and FIG. 3, and a second main surface 3. In the embodiment shown, said second main surface 3 is completely comprised of a gas tight material 4. Said first main surface 2 is partially made of gas tight material parts 5, 6 and a gas permeable material part 7. Said gas permeable material part 7 has a small pore size, such that permeation of bacteria and other harmful organisms is prevented, but that gas molecules are not hindered any way. The pore size therefore is smaller than 0.1 μm, preferably smaller than 0.05 μm.

In a condition ready for use, which is the situation wherein a user may place a product (not shown) that must be packaged sterile in said packaging 1, said both main surfaces 2, 3 of packaging 1 are mutually connected along part of their circumference. Preferably, parts of the packaging 1 are at their peripheral edges 8, 9, 10 as shown in FIGS. 2 and 3, mutually connected, allowing the user to place said product in said package through said open edge 11 into the packaging 1. Subsequently, the de peripheral edge 11 of packaging 1 may be closed, for example by means of heat sealing or an adhesive providing a gas tight connection.

The contents of the packaging then may be sterilized by subjecting the complete packaging with its contents to gamma radiation. Alternatively, a sterilizing gas may be brought into the packaging such that harmful organisms are killed. To that end, the packaging 1 may be subjected to an evacuation treatment such that gas that is already present in the packaging, substantially air, is removed through material part 7 from the packaging. Subsequently, a sterilizing gas may be brought into the packaging 1 through material part 7, so as to kill organisms that are already present in the packaging. This provides an effective sterilization treatment.

FIG. 2 shows a schematic view of a packaging 1. Only a first side 2 of packaging 1 is visible. So as to be able to easily re-move the contents from packaging 1 it is preferred that said material part 5 is releasably connected to at least one of the peripheral edges 8 and 9 with material part 4 (not shown in FIG. 2 and FIG. 3) as well to the connecting edge 12 with the gas permeable material 7. Advantageously, this connection is a peel off connection. It is especially preferred for the material part 5 to be connected releasably at the edges 8, 9 and 12, such that material part 5 is only fixedly connected along peripheral edge 11 to material part 4.

Material part 7 is preferably fixedly connected to material part 6, providing a high strength.

An alternative embodiment is obtained wherein material part 7 is fixedly connected to material part 5 along connecting edge 12. In that case, connecting edge 13 may be releasably, such that when opening packaging 1 material parts 5 and 7 are disconnected along edges 8, 9 and 13. Peripheral edge 11 remains connected, and as a consequence when unfolding same along the edge 11 a large sterile working space is obtained, comprised of the inside of material parts 5, 7 and 4 (see FIG. 1). Upon disconnecting material part 7 from material part 6 it is preferred that material part 7 remains connected to the outside of material part 6, providing an easy to catch edge and easing disconnecting same. The actual seal connection between material parts 7 and 6 may be provided at some distance, for example one centimeter, away from the edge of material part 7.

FIG. 3 shows an alternative embodiment of packaging 1. In this figure, a hand grip 14 has been shown. Since material part 6 and 7 are mutually fixedly connected and also are fixedly connected to material part 4 (not shown in FIG. 2 and FIG. 3), a sturdy construction is obtained and as a consequence, the packaging will not tear or break otherwise when transporting said packaging by handgrip 14.

The invention is not limited to the embodiments as mentioned above and as shown in the drawing. The invention is limited only by the appending claims.

The invention also embodies all and every combination of features and measures that have been described herein independently of each other.

What is claimed is:

1. A packaging (1) for sterile packaging a product, comprising a bag shaped body (1) comprising two main surfaces (2, 3) that are connected mutually gastight at at least part of their peripheral edges (8, 9, 10, 11) comprising a for gas non-permeable material (4, 5, 6), wherein at least part of said main surfaces (2, 3) comprises a gas permeable material part of a pore size that locks out harmful organisms, and gastight material part (5) that is positioned between two peripheral edges (8, 9) that extend in a longitudinal direction and between said gas permeable material part (7) and a peripheral edge (11) that extends in a transverse direction, wherein said gas tight material part (5) is releasably connected to said peripheral edges (8, 9) that extend in a longitudinal direction and to said gas permeable material (7) or wherein said gas permeable material (7) is fixedly connected to said gas tight material part (5) and releasably connected to said gas tight material part (6), and wherein said gas permeable material part (7) and said gas tight material part (5) are releasably connected at peripheral edges (8, 9).

2. The packaging according to claim 1, wherein said peripheral edge comprises a foldable edge.

3. The packaging according to claim 1, wherein said gas permeable material part is positioned at an inside of said gas tight material part and at a distance from the peripheral edge of said gas permeable material part has been connected thereto.

4. The packaging according to claim 1, wherein the releasable connection comprises a peelable connection.

5. The packaging according to claim 1, wherein a part of the peripheral edge of said main surface furthermore comprises a material that is sealable with said other main surface.

6. The packaging according to claim 5, wherein said sealable material comprises a heat sealable material.

7. The packaging according to claim 1, wherein said two edges that extend in a longitudinal direction are two opposite longitudinal edges of said packaging.

8. The packaging according to claim 7, wherein said gas permeable surface extends substantially between two longitudinal edges of said packaging along the width of a first main surface of said packaging.

9. The packaging according to claim 1, wherein said peripheral edge of said packaging extending in a transverse direction is embodied for providing a fixed connection of said both main surfaces.

10. The packaging according to claim 9, wherein said transverse peripheral edge of said packaging provides a fixed connection of said both main surfaces by means of heat sealing.

11. The packaging according to claim 1, wherein said packaging alongside said gas permeable material part, at the side opposite said releasably connected material parts, comprises a grip device for carrying the packaging.

12. A sterile closed packaging according to claim 1, comprising a sterile product.

13. A method for sterile packaging a product in a packaging of claim 1, the method comprising the steps of:

providing said packaging of claim 1;
placing in said packaging through a non-connected peripheral edge said product that is to be sterile packed;
mutually connecting said non-connected peripheral edges; and
sterilizing said product in said packaging.

14. The method according to claim 13, further comprising at least one of the steps of:

subjecting to gamma radiation at least said product; and
entering a sterilization gas into said packaging through said gas permeable surface.

15. The method according to claim 13, wherein sterilizing comprises the steps of evacuating said packaging and subsequently entering a sterilization gas through said gas permeable surface.

16. A method for removing a sterile product from a sterile packaging of claim 12, the method comprising the steps of:

releasing a part of said both main surfaces along a peripheral edge of said packaging;
releasing a connection edge of said gas tight material part with said gas permeable material part or a connection edge of said gas permeable material part with a material part that is connected thereto;
unfolding said packaging along a non-released peripheral edge to produce an opened packaging; and
removing said sterile product from said opened packaging.

17. The method according to claim 16, wherein said released part of a first main surface of said packaging remains connected with said other main surface along said non-released peripheral edge.

* * * * *